United States Patent
Lee et al.

(10) Patent No.: US 12,140,558 B2
(45) Date of Patent: Nov. 12, 2024

(54) BIOSENSOR USING FET ELEMENT AND EXTENDED GATE, AND OPERATING METHOD THEREOF

(71) Applicant: KOREA ELECTRONICS TECHNOLOGY INSTITUTE, Seongnam-si (KR)

(72) Inventors: Kook Nyung Lee, Seoul (KR); Woo Kyeong Seong, Seongnam-si (KR); Won Hyo Kim, Yongin-si (KR)

(73) Assignee: KOREA ELECTRONICS TECHNOLOGY INSTITUTE, Seongnam-si (KR)

( * ) Notice: Subject to any disclaimer, the term of this patent is extended or adjusted under 35 U.S.C. 154(b) by 159 days.

(21) Appl. No.: 17/139,576

(22) Filed: Dec. 31, 2020

(65) Prior Publication Data
US 2021/0318264 A1 Oct. 14, 2021

(30) Foreign Application Priority Data
Apr. 13, 2020 (KR) .................. 10-2020-0044765

(51) Int. Cl.
*G01N 27/414* (2006.01)
*G01N 33/543* (2006.01)

(52) U.S. Cl.
CPC ..... *G01N 27/4145* (2013.01); *G01N 33/5438* (2013.01)

(58) Field of Classification Search
CPC .................. G01N 27/4145; G01N 33/5438
See application file for complete search history.

(56) References Cited

U.S. PATENT DOCUMENTS

| | | | |
|---|---|---|---|
| 10,739,305 B1* | 8/2020 | Bhansali | G01N 33/48707 |
| 2012/0286803 A1* | 11/2012 | Nackaerts | G01N 27/414 |
| | | | 257/253 |
| 2016/0202208 A1* | 7/2016 | Lee | G01N 27/4145 |
| | | | 506/14 |
| 2016/0320332 A1* | 11/2016 | Hsiung | G01N 27/327 |

(Continued)

FOREIGN PATENT DOCUMENTS

| | | |
|---|---|---|
| KR | 10-2008-0027041 A | 3/2008 |
| KR | 10-1616560 B1 | 4/2016 |
| KR | 10-2019-0004980 A | 1/2019 |

OTHER PUBLICATIONS

Sarangadharan et al., Rapid detection of NT-proBNP from whole blood using FET based biosensors for homecare, Sensors and Actuators B: Chemical, 2019, 285, 209-215 (Year: 2019).*

(Continued)

*Primary Examiner* — Luan V Van
*Assistant Examiner* — Shizhi Qian
(74) *Attorney, Agent, or Firm* — Hauptman Ham, LLP (57) ABSTRACT

A bio sensor using a FET element and an extended gate, and an operating method thereof are disclosed. A biosensor using a field effect transistor (FET) device and an extended gate electrode according to the present invention is characterized by comprising: an extended gate electrode connected to the FET element; a sensing electrode made of the same material as the extended gate electrode and on which a receptor antibody selectively recognizing a target molecule is fixed; and a reference electrode that maintains a constant potential and is selectively connected to the sensing electrode.

3 Claims, 9 Drawing Sheets

(56) References Cited

U.S. PATENT DOCUMENTS

2019/0204321 A1* 7/2019 Lee ................... G01N 27/414
2019/0376926 A1* 12/2019 Tarasov ............. G01N 27/4145

OTHER PUBLICATIONS

Liao et al., Electrical Double Layer Gated Field Effect Transistor Biosensors for the Quantitative Detection of Beta-Human Chorionic Gonadotropin, ECS Transactions, 2019, 92 (6), 57-60 (Year: 2019).*
Sukesan et al., Instant Mercury Ion Detection in Industrial Waste Water with a Microchip Using Extended Gate Field-Effect Transistors and a Portable Device, Sensors, 2019, 19, 2209 (Year: 2019).*
Huang et al., Preparation of TiO2 nanowire arrays through hydrothermal growth method and their pH sensing characteristics, Japanese Journal of Applied Physics, 2014, 53, 06JG02 (Year: 2014).*
Wang et al., Heavy metal ion detection from whole blood using ion selective FET sensor, ECS Transactions, 2018, 85(9) 61-65 (Year: 2018).*
Korean Office Action issued on Jul. 28, 2021, in connection with the Korean Patent Application No. 10-2020-0044765.

* cited by examiner

BIOSENSOR USING FET ELEMENT AND EXTENDED GATE, AND OPERATING METHOD THEREOF

CROSS REFERENCE TO RELATED APPLICATIONS

Pursuant to 35 U.S.C. § 119 (a), this application claims the benefit of earlier filing dates and rights of priority to Korean Patent Application No.: 10-2020-0044765 filed on Apr. 13, 2020, the contents of which are hereby incorporated by reference in their entirety.

TECHNICAL FIELD

The present invention relates to a bio sensor using a FET element and an extended gate, and an operating method thereof, and more specifically, to a bio sensor using a FET element and an extended gate, and an operating method thereof, capable of measuring only the signal change due to the charge of the target biomolecule without being affected by the pH (hydrogen ion index) and ion concentration of a sample solution, and in particular, capable of eliminating the phenomenon of sensitive reaction to changes in pH.

BACKGROUND ART

In general, a bio sensor refers to an electrochemical sensor that can selectively detect a substance to be analyzed by combining a biological/chemical receptor that has a function of recognizing a target substance such as enzyme, antibody, deoxyribonucleic acid (DNA), and the like that has a specific function of an organism with a signal converter, thereby converting biological interactions and cognitive reactions into electrical signals, and through this, quick quantification of the concentration of various bioactive substances becomes possible therefore the device is expected to be widely used in bio, chemical, and environmental applications depending on the type of target substance.

In order to detect and analyze a target substance using an electrochemical sensor, it must have high sensitivity so that the signal change can appear large even with the fine characteristics of the target substance, and it must have chemical stability that can withstand the chemical composition of body fluids and physical stability that is not affected by fluid flow. In addition, for economy and practicality, an existing measurement platform must be available, and manufacturing must be easy to enable mass production.

Recently, as a device most suitable for the requirements of such an electrochemical sensor, a field effect transistor (FET) based biosensor manufactured by a microfabrication technology such as an integrated circuit process becomes the focus of interest.

In a FET based biosensor, the surface charge density of the channel changes as the target substance physically/chemically binds to the receiving substance (receptor) resulting in a change in a semiconductor inversion layer or Schottky barrier, thereby causing a change in the channel current which is to be measure.

By the way, while a general FET based biosensor is capable of non-labeled/ultra-high sensitivity measurement by the detection principle of an electric charge measurement method, since it has an inherent limitation in that the signal is generated by the pH (hydrogen ion index) or salt of the standard reagent (background solution) containing the biological sample and the surface charge of the target substance, there is a problem in that there are many difficulties in removing noise due to these factors.

PRIOR ART LITERATURE

Patent Literature (Patent Document 1) Korean Unexamined Patent Publication No. KR10-2008-0027041 (Publication date: Mar. 26, 2008)

DETAILED DESCRIPTION OF THE INVENTION

Technical Subject

An objective of the present invention devised to solve the above-described problem is to provide a bio sensor using a FET element and an extended gate, and an operating method thereof capable of measuring only the signal change due to the charge of the target biomolecule without being affected by the pH (hydrogen ion index) and ion concentration of a sample solution, and in particular, capable of eliminating the phenomenon of sensitive reaction to changes in pH.

Technical Solution

A biosensor using a FET element and an extended gate electrode according to an aspect of the present invention for achieving the above objective is characterized by comprising: an extended gate electrode connected to the FET element; and at least one sensing electrode made of the same material as the extended gate electrode and on which a receptor antibody selectively recognizing a target molecule is fixed, wherein the extended gate electrode and the sensing electrode are in contact with a solution, and wherein a driving potential is applied to the sensing electrode to pass through the solution and the extended gate electrode and transferred to the gate electrode of the FET element.

At this time, a driving potential applied to the sensing electrode through series connection of a first potential formed at an interface between the sensing electrode and the solution and a second potential formed at an interface between the solution and the extended gate electrode is transferred to the gate electrode of the FET element.

The aforementioned biosensor may further include a reset switch for selectively grounding the extended gate electrode.

In addition, the sensing electrode and the reference electrode may be formed of a module detachably coupled to a body including the extended gate electrode.

In addition, the sensing electrode may be formed of a module detachably coupled to a body including the reference electrode and the extended gate electrode.

In addition, a plurality of sensing electrodes is provided, and at least one of the plurality of sensing electrodes is used as a reference electrode in which a potential between the solution and an electrode interface is kept constant.

In addition, a plurality of the sensing electrodes is formed as an array, and a receptor antibody that peculiarly captures a metabolite of a cell may be fixed to each of the sensing electrodes.

The aforementioned biosensor may further include a connection switch for selectively applying a driving voltage to any one of the plurality of sensing electrodes.

In this case, each of the sensing electrode and the reference electrode may be formed as a module detachably coupled to a body including the extended gate electrode.

A biosensor using a FET element and an extended gate electrode according to another aspect of the present invention for achieving the aforementioned objective is characterized by comprising: an extended gate electrode connected to the FET element; a sensing electrode made of the same material as the extended gate electrode and on which a receptor antibody selectively recognizing a target molecule is fixed; and a switch for selectively applying a reference voltage to the sensing electrode.

A biosensor using a FET element and an extended gate electrode according to yet another aspect of the present invention for achieving the aforementioned objective is characterized by comprising: an extended gate electrode connected to the FET element; a plurality of sensing electrodes, each of which is made of the same material as the expansion gate electrode, and to which a receptor antibody peculiarly capturing a metabolite of a cell is fixed thereto; and a switch sequentially applying a reference voltage to each of the sensing electrodes.

A method of operating a biosensor according to an aspect of the present invention for achieving the above object, in the method of operating a biosensor using a FET element and an extended gate electrode, is characterized by comprising the steps of: connecting at least one sensing electrode to which a receptor that peculiarly captures a metabolite of a cell is fixed to a body including the extended gate electrode; measuring IV of the FET element by applying a reference voltage to the sensing electrode; and analyzing a potential change due to adsorption of the metabolite, wherein when a plurality of the sensing electrodes are connected, in the step of measuring the IV of the FET element, the reference voltage is sequentially applied to each of the sensing electrodes, and in the step of analyzing a potential change due to the adsorption of the metabolite is to compare and analyze the degree of shift of the measurement result of IV for each sensing electrode including the reference electrode to analyze the pH, ion concentration, or adsorption concentration of the target molecule.

Advantageous Effects

According to the invention, by canceling out any change in pH (hydrogen ion index) or change in ion concentration other than that of the target molecule, it is possible to measure only the signal change caused by the charge of the target biomolecule without being affected by the pH and ion concentration of the sample solution.

In addition, according to the present invention, it is possible to correct or interpret the sensing result by measuring the effect of noise on the pH of the sample through the reference electrode.

In addition, according to the present invention, the sensing module can be used for single use through the detachably coupled sensing module.

In addition, according to the present invention, since only the extended gate electrode of the body is exposed and the element is not exposed to the external environment, cleaning and maintenance are easy when the element is reused.

In addition, according to the present invention, the switch connected to the extended gate electrode has the advantage of protecting the FET element by grounding the electrically floating extended gate electrode when cleaning or maintaining it.

BEST MODE

Hereinafter, some embodiments of the present invention will be described through exemplary drawings. When referring to elements of each drawing, the same elements are denoted by the same reference numerals as much as possible, even if they are indicated on different drawings. In addition, in describing an embodiment of the present invention, if it is determined that a detailed description of a related known configuration or function interferes with an understanding of the embodiment of the present invention, a detailed description thereof will be omitted.

In addition, terms such as first, second, A, B, (a), and (b) may be used in describing the components of the embodiment of the present invention. These terms are only for distinguishing the component from other components, and the nature, order, or sequence of the component is not limited by the term. When a component is described as being "connected", "coupled" or "interconnected" to another component, the component may be directly connected, coupled or interconnected to the other component, but it should be understood that another component may be "connected", "coupled" or "interconnected" between the component and the other component.

Figure 1:
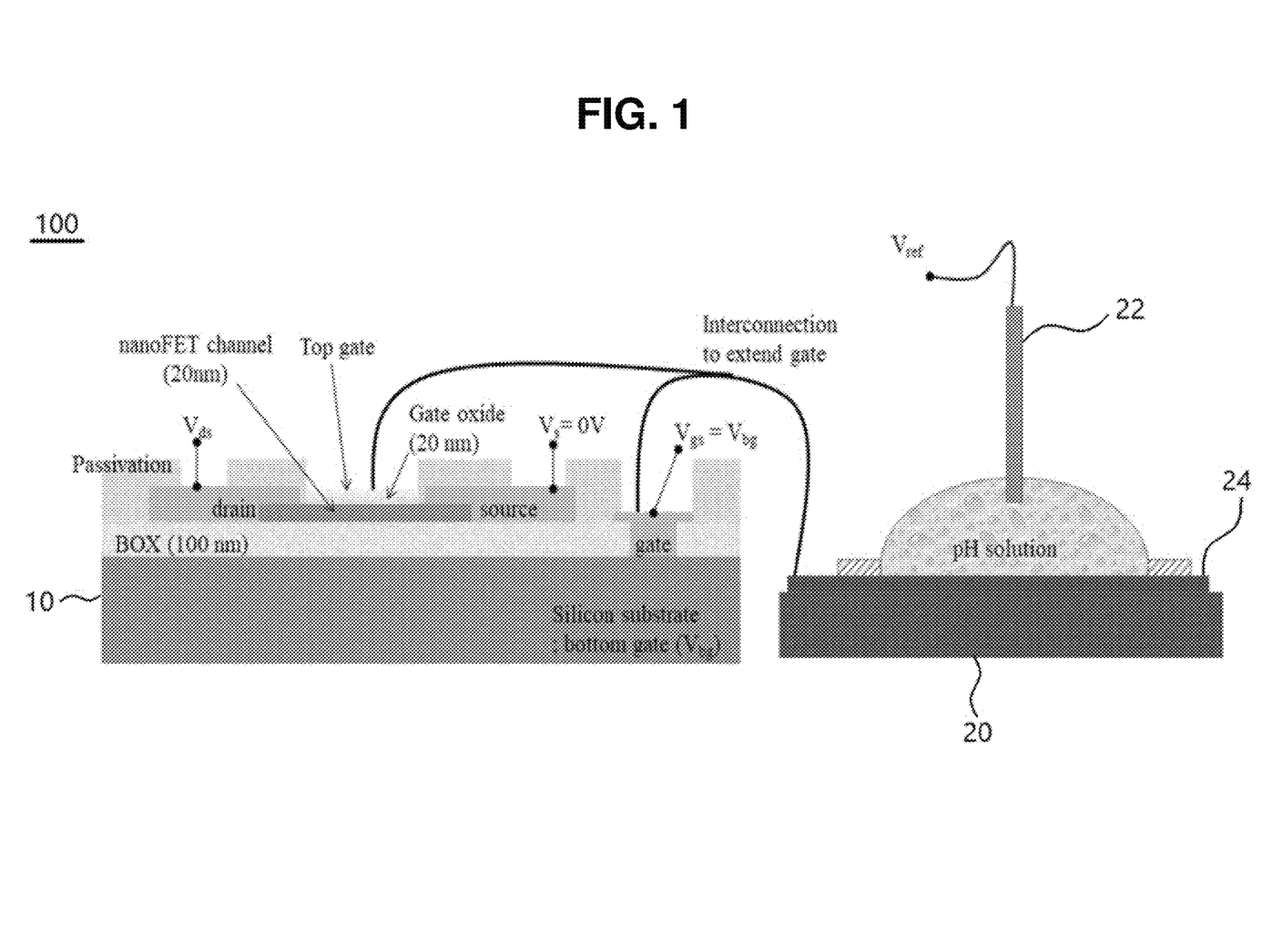
FIG. 1 is a diagram illustrating the connection of a FET element, an extension gate electrode, and a reference electrode of a FET biosensor.

FIG. 1 is a diagram illustrating the connection of a FET element 10, an extension gate electrode 24, and a reference electrode 22 of a FET biosensor 100. Here, as the FET element 10, a nano FET element manufactured on a silicon on insulator (SOI) substrate may be used. At this time, by applying a constant voltage Vds to the drain of the nano FET element and detecting a change in the magnitude of the drain-source current Ids, the amount of charge accumulated in the gate electrode and the polarity of the charge can be measured. Also, the gate voltage Vg may determine the threshold voltage Vth of the nano FET element.

The FET biosensor 100 is configured by connecting the extended gate electrode 24 of the extended electrode body 20 to the top gate of the nano FET element 10. At this time, a receptor or antibody that induces a peculiar reaction with the target molecule is immobilized on the extended gate electrode 24 so that the target molecule is adsorbed on the electrode surface. In this way, in order to observe the target molecules adsorbed on the electrode surface, the FET biosensor 100 is installed so that the reference electrode 22 is in contact with the solution placed on the extended gate electrode 24. In this case, the principle is that in order to measure the potential change due to adsorption of the target molecule, the FET biosensor 100 measures the threshold voltage shift of the nano FET element 10 using Vbg of the bottom gate electrode the nano FET element 10, and this is subject to correlation analysis with target molecule concentration for quantitative detection. That is, in this method, the FET biosensor 100 measures the change in the threshold voltage of the nano FET element caused by the adsorption of the target biomolecule adsorbed on the extended gate electrode 24 by sweeping the voltage of the bottom gate electrode of the nano FET element 10.

Figure 2:
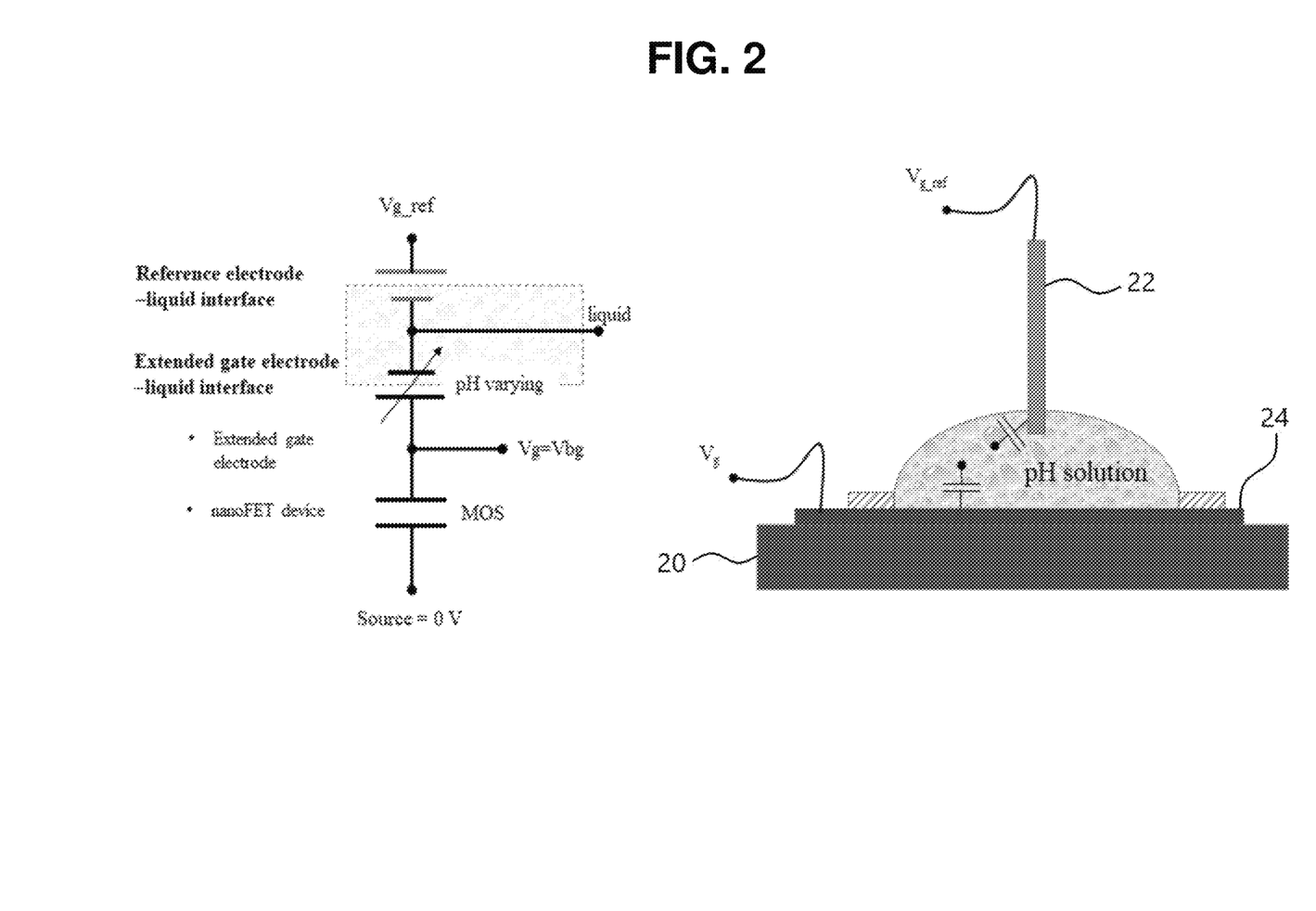
FIG. 2 is a diagram illustrating an equivalent circuit model showing the detection principle of the FET biosensor shown in FIG. 1.

FIG. 2 is a diagram illustrating an equivalent circuit model showing the detection principle of the FET biosensor shown in FIG. 1.

In FIG. 1, the interface between the reference electrode 22 and the solution, and between the solution and the extended gate electrode 24 can be expressed as a polar capacitor, and the principle of detecting a change in pH of a solution, change in ion concentration, and change in concentration of a target biomolecule can be explained through an equivalent circuit.

That is, when the pH of the test sample is changed, Ag/AgCl is used as the reference electrode 22, and when an indium tin oxide (ITO) electrode, which is a kind of metal oxide material, is used as the extended gate electrode 24, the surfaces of the two electrodes being in contact with the solution can be represented by polar capacitors. At this time, the reference voltage Vref may be expressed as a structure in which two polar capacitors are connected in series and connected to the gate of the nano FET element. In this case, since the reference voltage Vref is distributed by the two polar capacitors and the capacitor of the nano FET element, the voltage Vg of the gate electrode is changed by the size change of the polar capacitor, and the change in the size of the polar capacitor appears as a change in Ids, so this can be monitored.

In addition, when the reference electrode 22 is Ag/AgCl, there is no change in the polar capacitor due to the change in pH, and only the change in the polar capacitor at the interface between the solution and the extended gate electrode 24 appears, changes in pH value can be monitored through Ids change by gate voltage Vg.

Also, if the two electrodes are made of the same material, the change in the polar capacitor cancels each other, and since the voltage Vg of the gate electrode is always maintained at a constant value, noise due to pH can be removed. That is, depending on the use of materials for the reference electrode 22 and the extended gate electrode 24, the pH change may be effectively measured or a signal caused by the pH may be canceled to be removed.

Meanwhile, the FET biosensor 100 needs to selectively detect a target molecule that is a bio-marker. A typical FET biosensor modifies the surface of a gate electrode to fix an antibody or DNA strand corresponding to a receptor, and when a target molecule is selectively adsorbed thereto, it detects using Ids, which is a change in conductivity of a nanochannel. This method has a problem in that it is difficult to avoid the effect of noise due to the components of the sample because Ids changes not only by adsorption of target molecules but also by pH change or ion concentration change.

Figure 3:
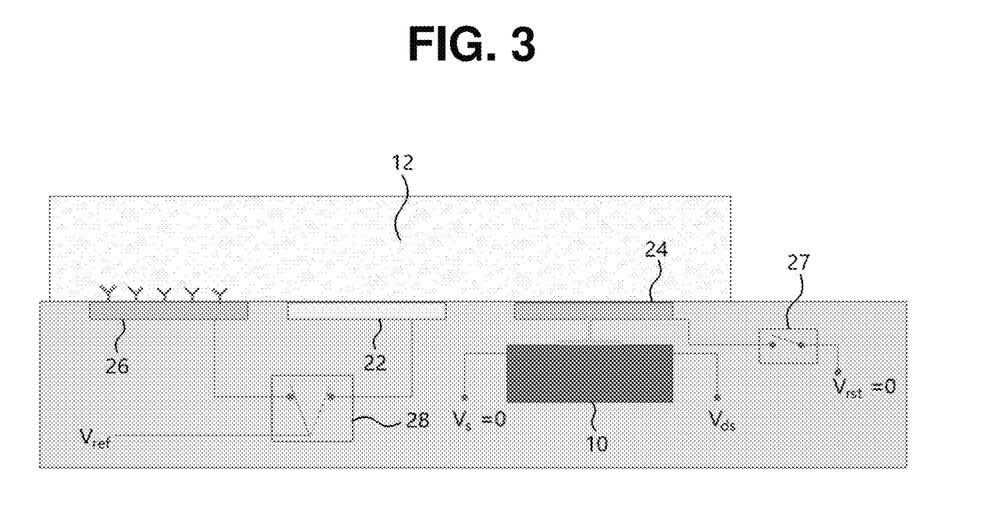
FIG. 3 is a schematic diagram illustrating a biosensor using an FET element and an extended gate electrode according to an embodiment of the present invention.

FIG. 3 is a schematic diagram illustrating a biosensor using an FET element and an extended gate electrode according to an embodiment of the present invention. The biosensor using the FET element and the extended gate electrode according to an embodiment of the present invention provides a method for effectively removing environmental noise signals caused by pH or ion concentration of an electrolyte solution.

Referring to FIG. 3, a biosensor using the FET element and the extended gate electrode according to the embodiment of the present invention comprises: a reference electrode 22 made of Ag/AgCl and maintaining a constant electric potential; an extended gate electrode 24 connected to the gate of the nano FET element 10, and a sensing electrode 26 made of the same material as the extended gate electrode 24. In addition, a biosensor using the FET element and the extended gate electrode may include a reset switch 27 performing a reset function by selectively grounding the extended gate electrode 24, and a connection switch 28 for selectively applying a reference voltage (driving voltage) Vref to the sensing electrode 26. Here, the reference electrode 22, the extended gate electrode 24, and the sensing electrode 26 are illustrated to be integrally formed with the nano FET element 10, but the reference electrode 22, the extended gate electrode 24, and the sensing electrode 26 may be included in a body independent from the nano FET element 10.

In the biosensor using the FET element and the extended gate electrode according to the embodiment of the present invention, the respective surfaces of the reference electrode 22, the extended gate electrode 24, and the sensing electrode 26 are exposed so as to be in contact with the solution 12. At this time, the reference electrode 22 includes a plurality of sensing electrodes 26, and at least one of them may be used as the reference electrode 22 in which the potential between the solution and the interface of the corresponding electrode is kept constant. In addition, the sensing electrode 26 is immobilized with a receptor antibody that selectively recognizes the target molecule, and allows only the target molecule in the solution sample to be specifically adsorbed. In addition, the first potential formed at the interface between the sensing electrode 26 and the solution, and the second potential formed at the interface between the solution and the extended gate electrode 24 are connected in series, and the driving potential applied to the sensing electrode 26 by the series connection of the first potential and the second potential is transferred to the gate electrode of the FET element 10. In addition, the connection switch 28 may selectively apply a driving voltage to any one of the plurality of sensing electrodes 26.

As described in the equivalent circuit of FIG. 2, the electrode surface in contact with the solution 12 makes a polar capacitor at the solution-electrode interface, and the size thereof varies depending on the changes in the characteristics of the interface between the material of the sensing electrode 26 and the solution 12. At this time, since the reference electrode 22 has a constant potential, in order to measure the pH change, the reference voltage Vref can detect the pH change with the serial connection structure of a polar capacitor composed of the reference electrode 22, the solution 12, and the extended gate electrode 24.

In order to detect the target protein molecule in the solution sample 12, the extended gate electrode 24 and the sensing electrode 26 are made of the same material, and are subjected to the same blocking treatment, and it is preferable to fix the receptor antibody only on the sensing electrode 26. At this time, when the reference voltage Vref is applied to the sensing electrode 26, by a series connection structure of a polar capacitor consisting of a sensing electrode 26, a solution 12, and an extended gate electrode 24 on which the antibody is fixed, and the polar capacitor value between the sensing electrode 26 and the solution 12 varies according to the amount of adsorption of the target molecule, and thereby, the reference voltage Vref can detect target molecules by changing Ids. In this case, changes in pH or ion concentration other than that of the target molecule are canceled out and removed from the series connection structure of the polar capacitor because the material of the extended gate electrode 24 and the sensing electrode 26 are the same, thus effectively removing the noise signal.

Figure 4:
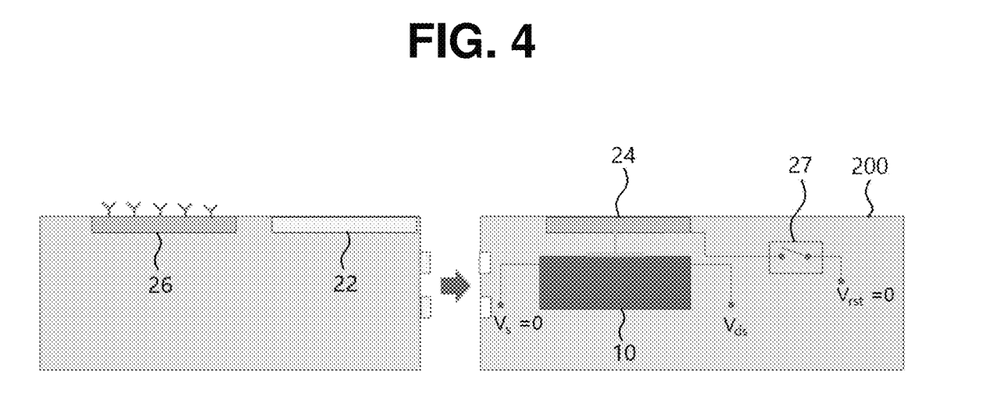
FIG. 4 is a schematic diagram illustrating a biosensor using an FET element and an extended gate electrode according to another embodiment of the present invention.

FIG. 4 is a schematic diagram illustrating a biosensor using an FET element and an extended gate electrode according to another embodiment of the present invention. The biosensor using the FET element and the extended gate electrode according to an embodiment of the present invention is configured in consideration of the characteristics of the biosensor to be used only once.

Referring to FIG. 4, the reference electrode 22 and the sensing electrode 26 may be formed as a module detachably coupled to a body 200 including an extended gate electrode 24. That is, since it is preferable to use the sensing electrode 26 of the FET biosensor for a single use, the biosensor using the FET element and the extended gate electrode according to the embodiment of the present invention allows the sensing electrode 26 can be replaced and used by forming the sensing electrode 26 as a module that is detachably coupled to a body that is to be used permanently. Here, in FIG. 4, the reference electrode 22 and the sensing electrode 26 are illustrated and described as being composed of a module that can be separated from the extended gate electrode 24, but the reference electrode 22 may be formed on the body 200 together with the extended gate electrode 24 or may be configured as a separate module that can be detachably coupled.

Through this, the biosensor using the FET element and the extended gate electrode according to the embodiment of the present invention can be used as a biosensor that detects hormones such as saliva or sex cortisol in saliva for each individual in the form of a toothbrush, or measures a pH change.

Figure 5:
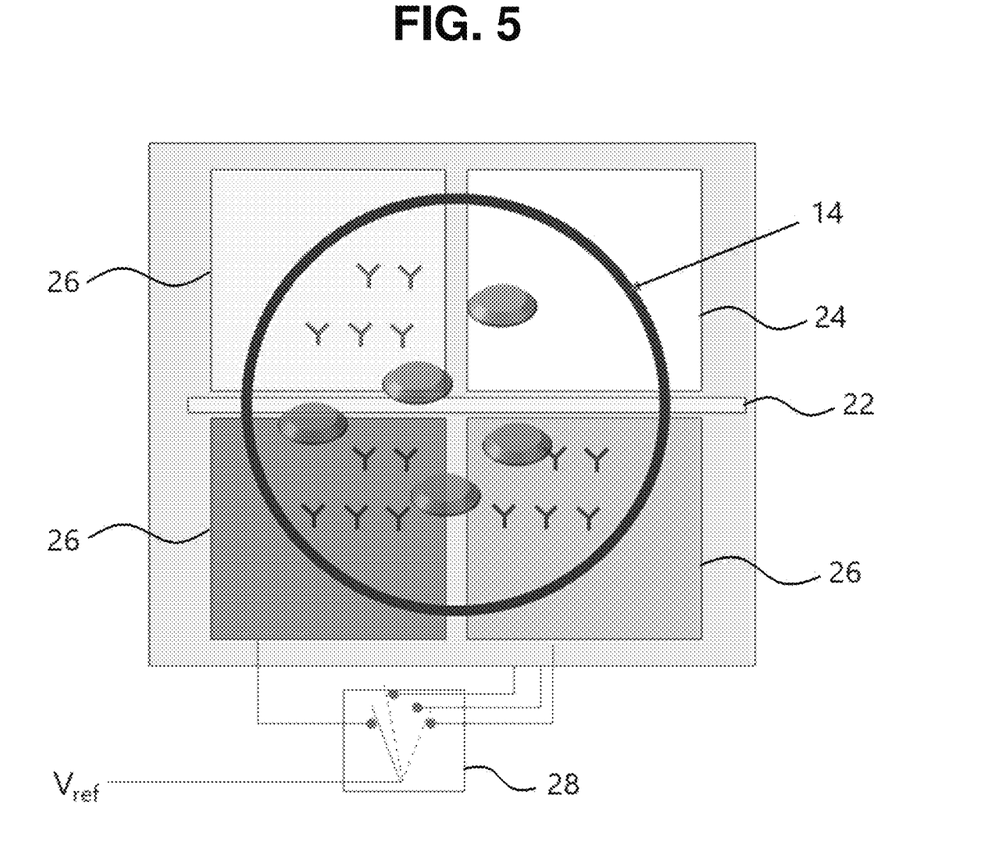
FIG. 5 is a schematic diagram illustrating a biosensor using an FET element and an extended gate electrode according to another embodiment of the present invention.

FIG. 5 is a schematic diagram illustrating a biosensor using an FET element and an extended gate electrode according to another embodiment of the present invention.

Referring to FIG. 5, a biosensor using a FET element and an extended gate electrode according to an embodiment of the present invention comprises a reference electrode 22, an extended gate electrode 24, a plurality of sensing electrodes 26, and a connection switch 28. At this time, each sensing electrode 26 may be composed of a module detachably coupled to a body in which the reference electrode 22 and the extended gate electrode 24 are installed. In addition, each sensing electrode 26 is composed of a module detachably coupled to a body in which the extended gate electrode 24 is installed together with the reference electrode 22, or each of the sensing electrodes 26 and the reference electrode 22 may be formed as independent modules to be detachably coupled to the body.

The plurality of sensing electrodes 26 are formed as an array, and a receptor antibody that peculiarly captures a metabolite of a cell is fixed to each sensing electrode 26. Here, the receptor antibody is a term used in the sense of peculiarly recognizing only the target antigen, and as for a receptor of each sensing electrode 26, anything that functions to selectively recognize only biomolecules or biochemical molecules other than antibodies can be used, that is, not only an antibody but also various biochemical materials such as aptamers and nucleic acids can be used. In addition, the solution chamber 14 containing the solution to be detected is installed so as to be in contact with the reference electrode 22, the extended gate electrode 24, and each sensing electrode 26. In this case, the connection switch 28 sequentially applies the reference voltage Vref to each sensing electrode 26, and as the reference voltage Vref is applied to each sensing electrode, it becomes possible to detect the target from the change in Vg and Ids of the nano FET element 10 owing to the configuration of the series connection structure of polar capacitor composed of a sensing electrode 26, a solution 14, and an extended gate electrode 24.

Figure 6:
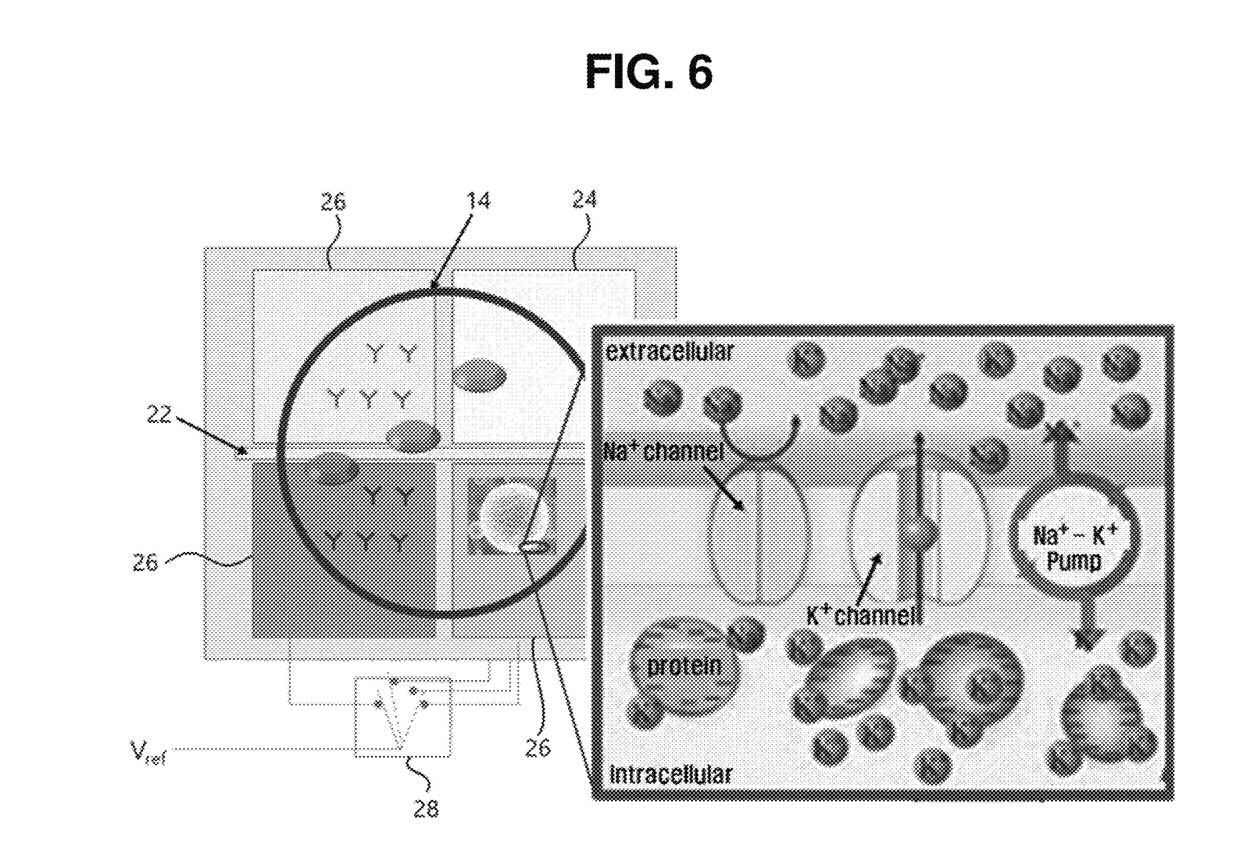
FIG. 6 is a diagram showing an example of detecting ions emitted from an ion channel of a cell membrane by the biosensor shown in FIG. 5.

FIG. 6 is a diagram showing an example of detecting ions emitted from an ion channel of a cell membrane by the biosensor shown in FIG. 5.

The biosensor using the FET element and the extended gate electrode according to the embodiment of the present invention immobilizes an antibody that peculiarly adsorbs a protein secreted from a cell on each sensing electrode 26, so that the situation in which ions are brought in or out of the cell from the cell membrane can be monitored with a nano FET element and a sensing electrode array. That is, each sensing electrode 26 is sequentially connected to the extended gate electrode 24 by the reference voltage Vref to measure the change in polar capacitance on the surface of the sensing electrode 26, and by simultaneously analyzing the change measured by each sensing electrode 26 with this change amount, it becomes possible to comprehensively analyze the change in pH, change in ion concentration, and change in concentration of target molecule. In addition, changes in each measurement can be measured using the principle of an equivalent circuit model as shown in FIG. 2, and events at the interface of the sensing electrode 26 can be monitored by IV measurement or real-time Ids change measurement.

Figure 7:
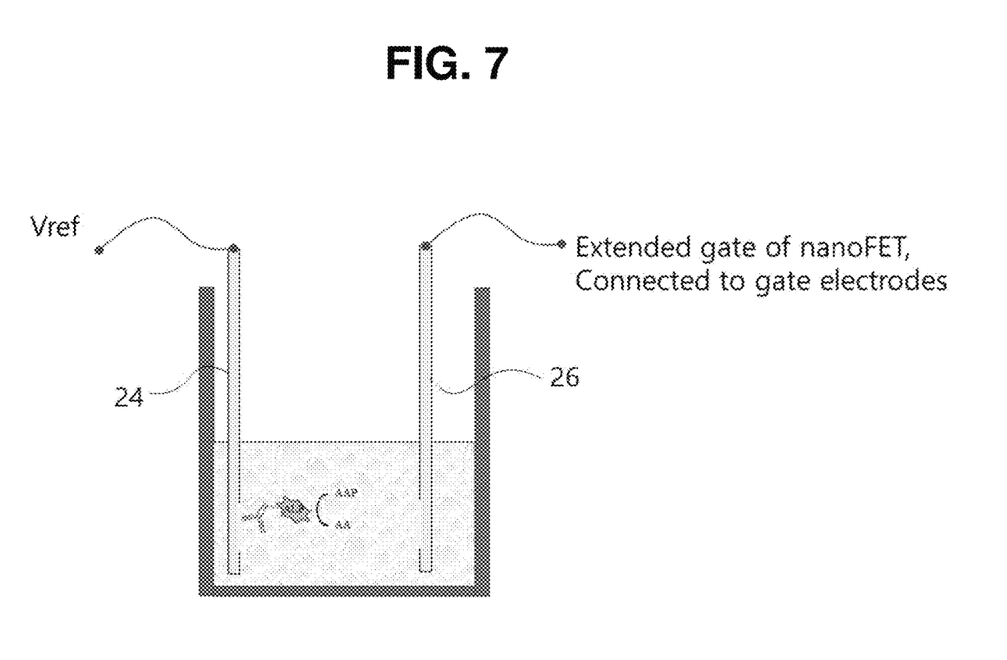
FIG. 7 is a diagram illustrating an example of applying an enzyme reaction product sensor accumulated on a surface of a sensing electrode as a biosensor using a FET element and an extended gate electrode according to another embodiment of the present invention.
Figure 8:
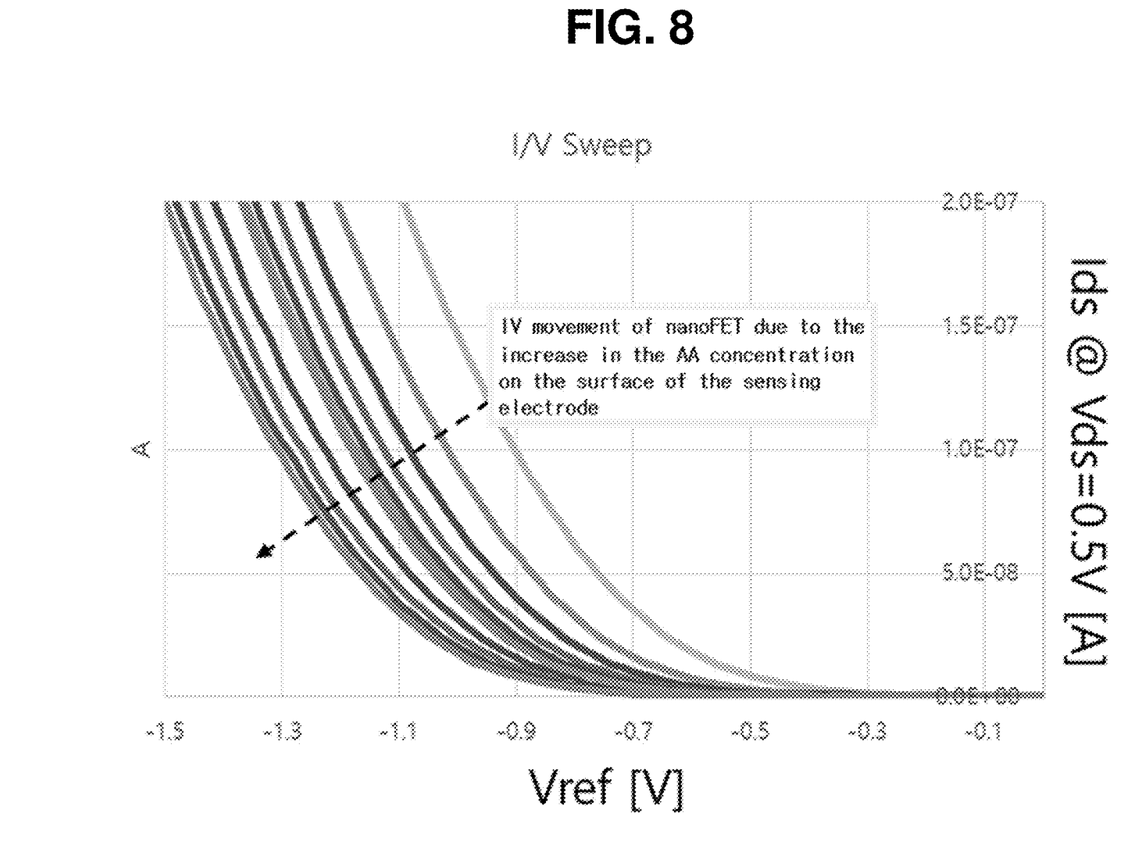
FIG. 8 is a view showing the result of measuring the IV shift according to the increase of the enzyme reaction product of FIG. 7.

FIG. 7 is a diagram illustrating an example of applying an enzyme reaction product sensor accumulated on a surface of a sensing electrode as a biosensor using a FET element and an extended gate electrode according to another embodiment of the present invention, and FIG. 8 is a view showing the result of measuring the IV shift according to the increase of the enzyme reaction product of FIG. 7.

The amount of the enzyme on the surface of the sensing electrode 26 is different depending on the concentration of the target molecule, and thus a difference may occur in the product of the enzyme reaction. Since the concentration of the enzyme reaction product increases and then saturates at the electrode surface according to the reaction time, as shown in FIG. 8, IV shift according to the increase of the enzyme reaction product can be measured using the biosensor according to the embodiment of the present invention. In addition to such an enzymatic reaction, a change in ion concentration, a change in pH, a change in surface potential, and the like, which can be locally changed on the sensing electrode surface, can also be measured using the biosensor according to an embodiment of the present invention.

Figure 9:
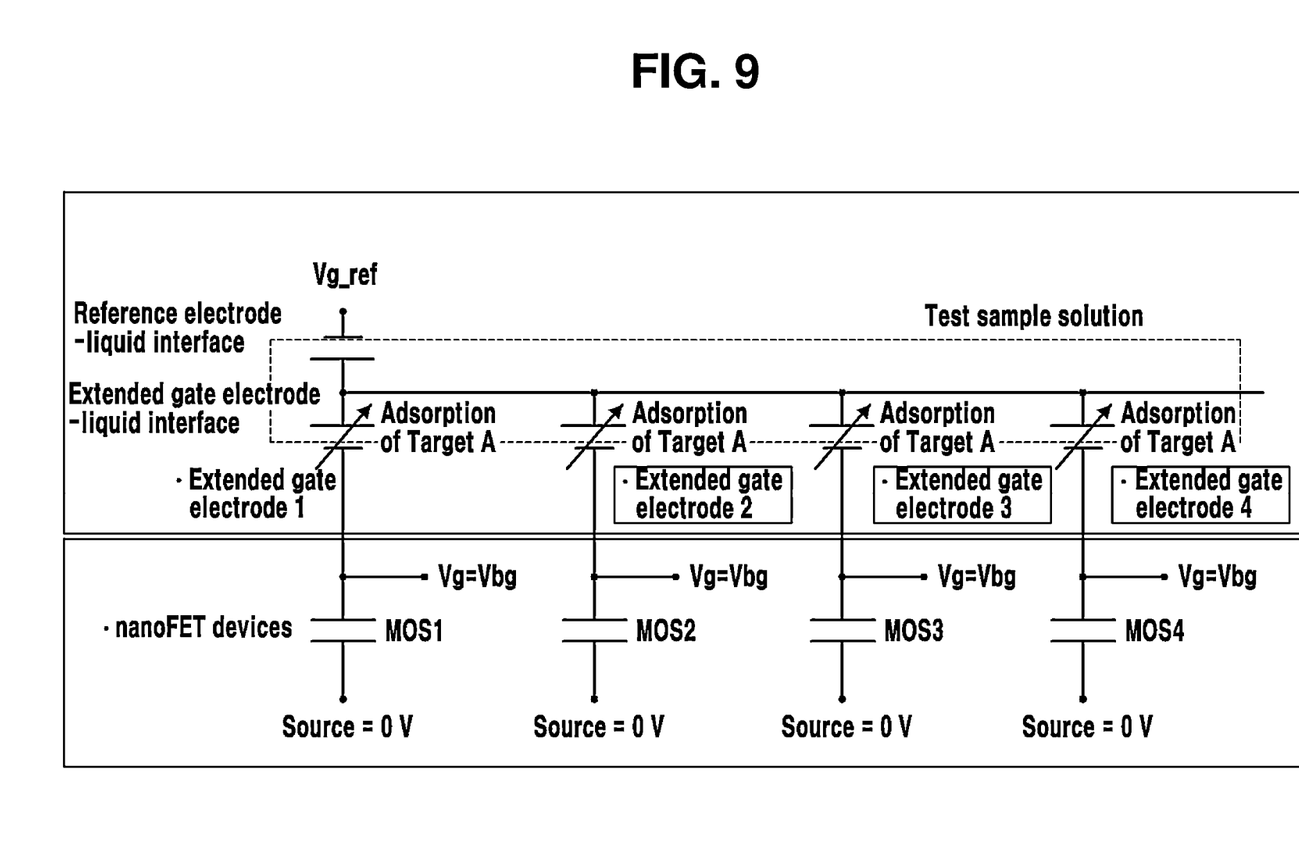
FIG. 9 is a diagram showing an equivalent circuit when a plurality of FET elements and a plurality of sensing electrodes are configured in parallel, respectively.

Meanwhile, the biosensor according to an embodiment of the present invention may be implemented using a plurality of FET devices and a plurality of sensing electrodes. In this case, each sensing electrode is preferably configured to correspond to each of a plurality of FET devices, and an equivalent circuit in this case is as illustrated in FIG. 9.

Figure 10:
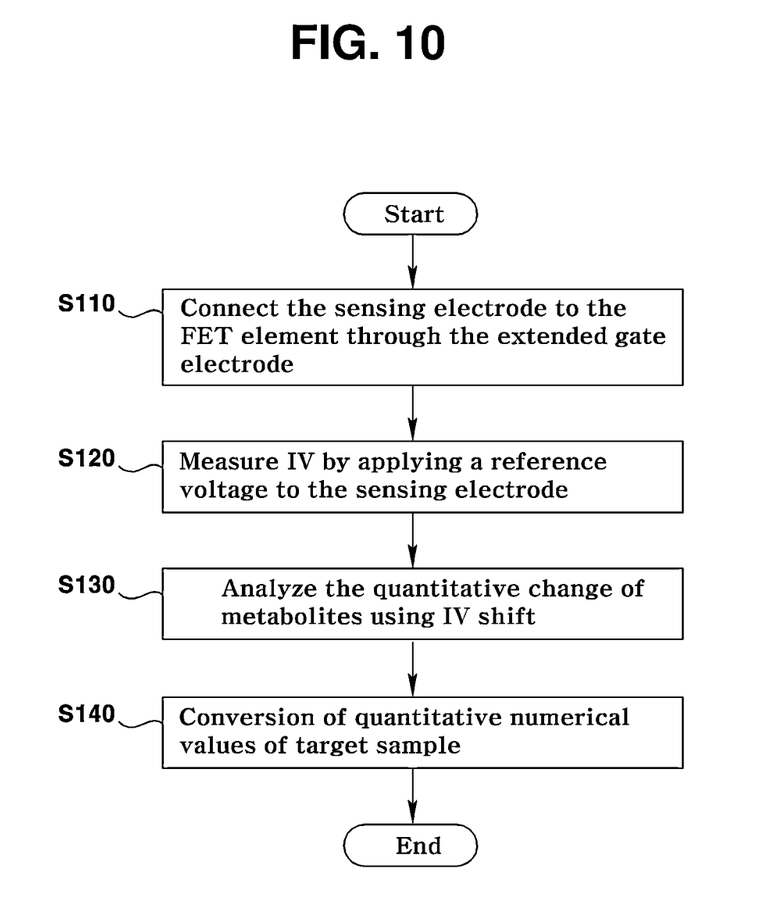
FIG. 10 is a flowchart showing a method of operating a biosensor according to an embodiment of the present invention.

FIG. 10 is a flowchart showing a method of operating a biosensor according to an embodiment of the present invention.

The method of operating the biosensor according to the embodiment of the present invention may be performed by the biosensor using the FET element and the extended gate electrode shown in FIGS. 3 to 8.

Referring to FIGS. 1 to 9, at least one sensing electrode 26 is connected to the FET element 10 through the extended gate electrode 24 (S110). At this time, the sensing electrode 26 is fixed with a receptor that peculiarly captures a metabolite of a cell, and may be formed in a plurality of arrays. In addition, the sensing electrode 26 may be formed as a module together with the reference electrode 22 or as a module independent from the reference electrode 22 to be detachably coupled to the body 200. In addition, the sensing electrode 26 may be integrally formed with the FET element 10 together with the reference electrode 22 and the extended gate electrode 24, and in this case, step S110 may be omitted.

Next, the reference voltage Vref is applied to the sensing electrode 26 to measure the IV of the FET element 10 (S120). In this case, when the sensing electrodes 26 are formed of a plurality of arrays, the reference voltage Vref is applied to each sensing electrode 26. In this case, the reference voltage Vref measures the Ids of the FET element 10 by sweeping the +Vg region from Vg, or Ids of the FET element 10 when each sensing electrode is connected through switching while maintaining it by applying a fixed voltage.

That is, when the reference voltage Vref is applied to the sensing electrode 26, the polar capacitor value between the sensing electrode 26 and the solution varies according to the adsorption amount of the target molecule due to the series connection structure of the polar capacitor consisting of the sensing electrode 26, the solution, and extended gate electrode 24. At this time, the nano FET element 10 may detect a target molecule by analyzing a potential change due to adsorption of metabolites due to Ids change (S130). In this case, changes in pH or ion concentration other than the target molecule are canceled and removed from the series connection structure of the polar capacitor because the material of the sensing electrode 24 and the extended gate electrode 24 are the same, and the noise signal can be effectively removed. Here, when the sensing electrodes 26 are formed in a plurality of arrays, by switching the reference voltage Vref and sequentially applying the reference voltage Vref to each sensing electrode 26, after sweeping the IV of each of the sensing electrodes 26 and the reference electrode 22, the results of sensing the pH according to the target concentration can be confirmed by comparing and analyzing them with each other. In addition, the amount of enzyme on the surface of the sensing electrode 26 is different according to the concentration of the target molecule, and thus, a difference may occur in the product of the enzyme reaction. Since the concentration of the enzyme reaction product increases and then saturates at the electrode surface according to the reaction time, the IV shift according to the increase in the enzyme reaction product may be measured and the target molecule may be detected using the biosensor according to an embodiment of the present invention. The detected result may be converted into a quantitative value of the target sample (S140). Such a biosensor can also be used as a monitoring sensor platform that measures cell reaction products while growing cells.

Although the embodiments according to the present invention have been described above, these are merely exemplary, and a person skilled in the art will understand that various modifications and equivalent scopes of embodiments are possible therefrom. Accordingly, the scope of protection of the present invention should be determined by the following claims as well as equivalents thereto.

The invention claimed is:

1. A biosensor, comprising:
a first module, comprising:
a field effect transistor (FET) element comprising a gate electrode;
an extended gate electrode connected to the gate electrode of the FET element; and
a first coupling; and
a second module, comprising:
at least one sensing electrode made of the same material as the extended gate electrode and on which a receptor antibody selectively recognizing a target molecule is fixed;
a reference electrode; and
a second coupling,
wherein
the first module and the second module are configured to be detachably combined to form an assembly by joining the first coupling and the second coupling,
the first module and the second module are free from electrical components that electrically connect the extended gate electrode with the at least one sensing electrode and the reference electrode in an assembled state in which the first module and the second module are combined to form the assembly, and
in the assembled state, the assembly comprises a surface extending from the first module to the second module configured to accommodate a solution that electrically connects the extended gate electrode with the at least one sensing electrode and the reference electrode such that, in response to a driving potential being applied to the at least one sensing electrode, the driving potential is communicated through the solution to the extended gate electrode and transferred to the gate electrode of the FET element by way of the extended gate electrode.

2. The biosensor according to claim 1, wherein the driving potential applied to the at least one sensing electrode is through a series connection of a first potential formed at an interface between the at least one sensing electrode and the solution and a second potential formed at an interface between the solution and the extended gate electrode.

3. The biosensor according to claim 1, further including:
a reset switch connected with the extended gate electrode and configured to selectively ground the extended gate electrode.

\* \* \* \* \*